US010799641B2

(12) United States Patent
Butler et al.

(10) Patent No.: US 10,799,641 B2
(45) Date of Patent: Oct. 13, 2020

(54) DRUG DELIVERY DEVICE

(71) Applicant: Sanofi, Paris (FR)

(72) Inventors: Joseph Butler, Rugby (GB); Anthony Paul Morris, West Midlands (GB); William Geoffrey Arthur Marsh, Buckinghamshire (GB); Matthew Meredith Jones, Warwick (GB)

(73) Assignee: Sanofi, Paris (FR)

( * ) Notice: Subject to any disclaimer, the term of this patent is extended or adjusted under 35 U.S.C. 154(b) by 731 days.

(21) Appl. No.: 15/533,771

(22) PCT Filed: Dec. 8, 2015

(86) PCT No.: PCT/EP2015/078927
§ 371 (c)(1),
(2) Date: Jun. 7, 2017

(87) PCT Pub. No.: WO2016/091854
PCT Pub. Date: Jun. 16, 2016

(65) Prior Publication Data
US 2017/0326301 A1  Nov. 16, 2017

(30) Foreign Application Priority Data
Dec. 8, 2014  (EP) ..................................... 14306958

(51) Int. Cl.
*A61M 5/315* (2006.01)
(52) U.S. Cl.
CPC .... *A61M 5/31536* (2013.01); *A61M 5/31533* (2013.01); *A61M 5/31561* (2013.01)

(58) Field of Classification Search
CPC .......... A61M 5/31536; A61M 5/31533; A61M 5/31535; A61M 5/31548; A61M 5/31561
See application file for complete search history.

(56) References Cited

U.S. PATENT DOCUMENTS

2008/0033369 A1* 2/2008 Kohlbrenner ..... A61M 5/31525
604/207

FOREIGN PATENT DOCUMENTS

JP  2002-505597  2/2002
JP  2012-521819  9/2012
(Continued)

OTHER PUBLICATIONS

International Preliminary Report on Patentability in International Application No. PCT/EP2015/078927, dated Jun. 13, 2017, 5 pages.
(Continued)

*Primary Examiner* — Manuel A Mendez
*Assistant Examiner* — Tasnim Mehjabin Ahmed
(74) *Attorney, Agent, or Firm* — Fish & Richardson P.C.

(57) ABSTRACT

A drug delivery device for selecting and dispensing a number of user variable doses of a medicament includes a housing having an opening, a dose selector operable to set a dose by rotation relative to the housing, a release member controlling movement of a piston in a dispensing direction, and a display comprising a units number wheel and a tens number wheel which are coupled to each other such that a continuous rotation of the units number wheel is translated into an intermittent rotary motion of the tens number wheel. The release member rotates, during dose dispensing, an angle corresponding to the dose set by the dose selector, thereby allowing a piston to move in a dispensing direction.

16 Claims, 4 Drawing Sheets

(56) References Cited

FOREIGN PATENT DOCUMENTS

| WO | WO 98/56436 | 12/1998 |
| WO | WO 01/87386 | 11/2001 |
| WO | WO 2010/112377 | 10/2010 |
| WO | WO 2014/166900 | 10/2014 |
| WO | WO 2014/166916 | 10/2014 |

OTHER PUBLICATIONS

International Search Report and Written Opinion in International Application No. PCT/EP2015/078927, dated Apr. 7, 2016, 8 pages.

\* cited by examiner

DRUG DELIVERY DEVICE

CROSS-REFERENCE TO RELATED APPLICATIONS

This application is a U.S. national stage application under 35 USC § 371 of International Application No. PCT/EP2015/078927, filed on Dec. 8, 2015, which claims priority to European Patent Application No. 14306958.1, filed on Dec. 8, 2014, the entire contents of which are incorporated herein by reference.

TECHNICAL FIELD

The present disclosure is generally directed to a drug delivery device suitable for selecting and dispensing a number of user variable doses of a medicament.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

WO 2014/166900 A1 discloses a spring driven drug delivery device with a dose setting member which is in splined and direct engagement with a dose indicating wheel. The dose indicating wheel is permanently coupled to a gear wheel which acts on a drive member interacting with the spring. A drive sleeve is operably releasable from a piston rod for switching the device between a dose setting mode and a dose dispensing mode.

WO 2014/166916 A1 discloses an injection device comprising an epicyclic gear box permanently coupling a dial grip to a units gear carrying number markings.

For dose accuracy reasons it is essential that the user may easily identify the actually set dose. Some devices comprise a number sleeve with a series of figures provided on a helical path on the outside of the number sleeve. The number sleeve is rotated during dose setting and dose dispensing, such that the actually set dose is visible through a window in the device. A possible drawback of such number sleeve displays is caused by the aim to minimize drug delivery devices, which results in smaller number sleeves and, thus, a smaller figure size which may be difficult to read for visually impaired users.

WO 98/56436 A1 discloses a drug delivery device with a dose setting element comprising a scale on the dose setting element for indicating the set dose.

WO 01/87386 A1 discloses a dose display comprising two flexible discs which each carry in a band along its perimeter numbers. A sprocket drum which is permanently coupled to a dose setting member has ten sprockets engaging sprocket holes in the units counting disc and one sprocket engaging sprocket holes in the tens counting disc. The flexible discs are cambered to fit into the cylindrical or rounded housing of the device. In an alternative embodiment one single flexible disc is provided which is permanently coupled to dose setting grip. The dose display of WO 01/87386 A1 requires that the dose setting member or grip rotates back during dose dispensing, which may be considered as disturbing or confusing for some users. In addition, in the embodiment with two discs the tens counting disc is not secured against unintended rotational movement when the sprocket is not engaging the sprocket hole. Thus, a misreading could occur if the tens counter disc moves unintended which results in poor dose accuracy.

SUMMARY

The present disclosure is directed to providing a drug delivery device allowing a reliable representation of the selected dose with improved ease of use.

Certain implementations of the disclosure can be implemented as a drug delivery device for selecting and dispensing a number of user variable doses of a medicament according to claim 1. The device may be a disposable device, i.e. a device which does not provide for an exchange of an empty cartridge. The device comprises a housing, e.g. with an aperture or window, a dose selector operable to set a dose by rotation relative to the housing, a release member controlling movement of a piston in a dispensing direction and a display with at least one number wheel or number sleeve, preferably comprising a units number wheel and a tens number wheel which are coupled to each other such that a continuous rotation of the units number wheel is translated into an intermittent rotary motion of the tens number wheel.

According to a first independent aspect of the disclosure the units number wheel is coupled to the tens number wheel by a gear mechanism, which preferably not only transfers a continuous rotation of the units number wheel into an intermittent rotary motion of the tens number wheel but may also prevent unintended movement of the tens number wheel. Such an unintended movement of the tens number wheel may be avoided, if, for example, the units number wheel comprises a raised circular blocking disc that locks the tens number wheel in position between the steps of intermittent rotary motion of the tens number wheel. The tens number wheel may have several concave contact faces which abut the raised circular blocking disc. The circular blocking disc may have a recess to allow movement of the tens number wheel as a units number wheel driving dog engages a corresponding driven dog of the tens number wheel.

According to a further independent aspect of the disclosure, the release member may rotate during dose dispensing an angle corresponding to the dose set by the dose selector thereby allowing a piston to move in a dispensing direction, wherein the device further comprises a clutch mechanism which rotationally couples the number wheel or number sleeve, preferably the units number wheel, to the dose selector and de-couples the number wheel or number sleeve, preferably the units number wheel, from the release member during dose setting and which rotationally de-couples the number wheel or number sleeve, preferably the units number wheel, from the dose selector and couples the number wheel or number sleeve, preferably the units number wheel, to the release member during dose dispensing. In other words, the number wheel or number sleeve, preferably the units number wheel, follows the rotation of the dose selector during dose setting, i.e. dialing up or down, while it follows the rotation of the release member during dose dispensing. Thus, the dose selector may be kept stationary during dose dispensing, while the display still shows the actually selected dose decreasing as the release member rotates. In this respect, the clutch mechanism is operable to be switched, preferably by an axial movement, between a dose setting position and a dose dispensing position, wherein, when the clutch mechanism is in its dose setting position, the number wheel or number sleeve is rotationally coupled via the clutch mechanism to the dose selector and the number wheel or number sleeve is rotationally de-coupled from the release member and wherein, when the the clutch mechanism is in its dose dispensing position, the number wheel or number sleeve is rotationally de-coupled from the dose selector and the number wheel or number sleeve is rotationally coupled via the clutch mechanism to the release member.

The idea of constraining a display member to the dose selector during dose setting and to constrain the display member to the release member during dose dispensing is applicable in a variety of different drug delivery devices irrespective of the drive mechanism of the device. For example, this disclosure may be used in spring driven devices as well as manually driven devices. Further, it is applicable in devices where a piston is axially pushed forward during dispensing by a spring or by a piston rod which may be axially and/or rotationally driven.

According to the disclosure, the device comprises at least a units number wheel and a tens number wheel. This allows displaying figures in a relatively large scale which are readable even for visually impaired persons. In addition, every single number of the selected dose may be displayed, which increases readability of the dose size compared with displays which only show every other number. The number wheels may be rigid discs each extending in a flat plane.

The housing may be a single unitary component or a multi-component part encasing and/or guiding other component parts. Preferably, the housing comprises an outer housing shell and a chassis or the like inner housing parts. A window or opening may be provided in the housing through which the number wheels can be seen for reading the displayed dose. A closed transparent window may include a lens to enlarge the displayed dose. It further prevents intrusion of dust or the like dirt into the device.

The dose selector (dial grip) and/or the release member may be disc-shaped or cup-shaped component parts rotatable with respect to the housing. Preferably, they are rotatable about a common axis. The piston may be guided in a cartridge and/or in the housing or a cartridge holder. Preferably, the piston is axially movable in a direction perpendicular to the axis of rotation of the dose selector and/or the release member.

A preferred embodiment of the disclosure comprises a Geneva drive (Maltese cross) mechanism. For example, the gear mechanism comprises a driving dog provided on the units number wheel and several corresponding driven dogs provided on the tens number wheel. Every time a (the) driving dog of the units number wheel engages a corresponding driven dog of the tens number wheel, the tens number wheel is rotated for a given increment which results in a stepwise rotational movement of the tens number wheel upon a continuous rotational movement of the units number wheel. Preferably, the units number wheel comprises one single driving dog and is provided with the FIGS. 0 to 9. As an alternative, the units number wheel comprises two driving dogs and is provided with the FIGS. 0 to 9 twice.

Preferably, the maximum settable dose is limited to a given value by a maximum dose stop feature. In addition, a zero unit dose stop feature may be provided which may also determine the end position of dose dispensing movements. For example, the drug delivery device may comprise a dose ring gear which is rotationally coupled to the dose selector during dose setting and which is rotationally coupled to the release member during dose dispensing. The dose ring gear may have a maximum dose stop feature and/or a minimum dose stop feature with corresponding counter stop(s) provided on a housing part or a component part which is rotationally constrained to the housing. In other words, the dose ring gear is allowed to rotate a predetermined degree with respect to the housing between end stop positions.

If the dose ring gear is permanently rotationally coupled to the units number wheel, the position of the dose ring gear relative to the zero unit stop and/or the maximum dose stop may be displayed by units number wheel and the tens number wheel.

The clutch may further rotationally couple the dose ring gear to the units number wheel, rotationally couple the dose ring gear to the dose selector and de-couple the dose ring gear from the release member during dose setting and rotationally couple the dose ring gear to the release member and de-couple the dose ring gear from the dose selector during dose dispensing. Thus, the clutch is a multi-function element coupling and de-coupling several different component parts. Preferably, the clutch and the release member each comprise at least one gear wheel.

According to a preferred embodiment of the disclosure the clutch comprises a clutch gear having a first gear wheel and a second gear wheel which is rotationally constrained to the first gear wheel, e.g. via a shaft portion.

It is preferred if the clutch gear is axially movable between a dose setting position, in which the first gear wheel is rotationally coupled to the dose selector and the units number wheel and in which the second gear wheel is rotationally coupled to the dose ring gear, and a dose dispensing position, in which the first gear wheel is rotationally coupled to the units number wheel and in which the second gear wheel is rotationally coupled to the dose ring gear and the release member. In the dose setting position, the second gear wheel is de-coupled from the release member and in the dose dispensing position the first gear wheel is de-coupled from the dose selector.

The clutch gear may be rotatable about a first axis wherein the dose selector, the dose ring gear and the release member are rotatable about a second common axis which is parallel to and offset from the first axis.

The drug delivery device may further comprise a trigger for actuating the clutch. The trigger may comprise a clutch lever pivot-mounted within the housing. Preferably, the clutch lever comprises a guiding sleeve at least partially surrounding a part of the clutch for axially displacing the clutch upon actuation of the trigger. The lever may be supported in the housing or a chassis of the housing such that actuation of the trigger causes an axial displacement of the guiding sleeve.

In a preferred embodiment the device is a spring driven device. The spring may be a compression spring which is charged (strained) during or prior to assembly of the device. As an alternative, the spring may be charged during dose setting. Preferably, the device is a disposable device with the spring being charged for life, i.e. allowing dispensing several variable user selectable doses until the device or its cartridge is empty. Thus, the forces required for dose setting and dose dispensing are relatively low.

The spring may act directly or indirectly on the piston. Preferably, a cable, belt or wire is attached with one of its ends to the piston and with its other end to a cable spool of the release member, such that upon rotation of the release member the piston is allowed to be pushed in the dispensing direction by the spring. As an alternative to a cable wound on a spool with a relatively small diameter, a toothed belt and a toothed belt drum may be used, wherein the belt is wrapped around approximately 75% of the belt drum. This may have advantages in terms of assembly and robustness in use.

To avoid uncontrolled release of the spring, the device may further comprise a stop element preventing rotation of the release member during dose setting and allowing rotation of the release member during dose dispensing.

Additional features like a clicker mechanism generating a tactile and/or audible feedback upon dose setting and/or dose dispensing or a last dose stop mechanism preventing setting of a dose which exceeds the amount of medicament remaining in the cartridge may be provided. For example, a dial clicker may be provided by a ring of teeth on the dose selector engaging a flexible finger e.g. on the chassis or outer housing shell. The dispense clicker may include the release member. As an alternative, a clicker may be provided by the dosing ring gear and a rotationally fixed component. A last dose stop feature may comprise a threaded shaft and a nut with one of the shaft or the nut being rotationally coupled to the dose selector while the other of the shaft and the nut is rotationally fixed. The threaded shaft and the nut may have corresponding stops preventing further relative rotation if a dose is set which exceeds the amount of medicament remaining in the cartridge. Thus, further rotation of the dose selector (in the dialing up direction) is prevented.

To avoid that the spring energy is not released in an unsafe manner, the order in which the clutch disengages and engages with the other release mechanism components is important.

According to a preferred embodiment, as the clutch lever moves from the dose setting position, it first locks the rotation of the dose selector by moving the dial clicker into a position whereby it requires a very high torque to dial either up or down. As the clutch lever continues to move it causes the clutch gear to axially engage the release member (release gear). The clutch and release gears may have chamfered teeth for ease of engagement to accommodate moulding and positional tolerances. As the clutch lever continues to move further, it causes the clutch gear to disengage from the dose selector so that the last dose mechanism is not rewound and the dose selector does not spin during dispense (preventing the user from jamming the device by touching it). Finally, the clutch lever causes the dose stop to disengage from the release member, allowing the release gear with the cable spool to rotate, releasing some cable and permitting the piston spring to move the piston.

The drug delivery device may comprise a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The disclosure relates to a mechanism for use in a medical device that can be operated to deliver variable, user-selectable doses of medicament from a cartridge, via a needle. The mechanism provides simple, push button trigger operation. A dose is set by rotating a dial grip located on the housing of the device and is injected by pushing the separate trigger button. The mechanism contains a factory pre-charged compression spring, the extension of which dispenses medicament and is controlled by the user via a spur gear-based release mechanism. The device provides audible, visual and tactile feedback both on setting and delivery of each dose.

This device is a disposable, user-selectable, variable dose pen injector that can be used with cartridges containing liquid medicament. It has a novel layout, and is particularly attractive for ergonomic reasons (comfortable to hold, a dose display with every dose number, compact, low setting torque, short button travel, and low dispense force).

BRIEF DESCRIPTION OF THE FIGURES

Non-limiting, exemplary embodiments of the disclosure will now be described with reference to the accompanying drawings, in which.

DETAILED DESCRIPTION

Figure 1:
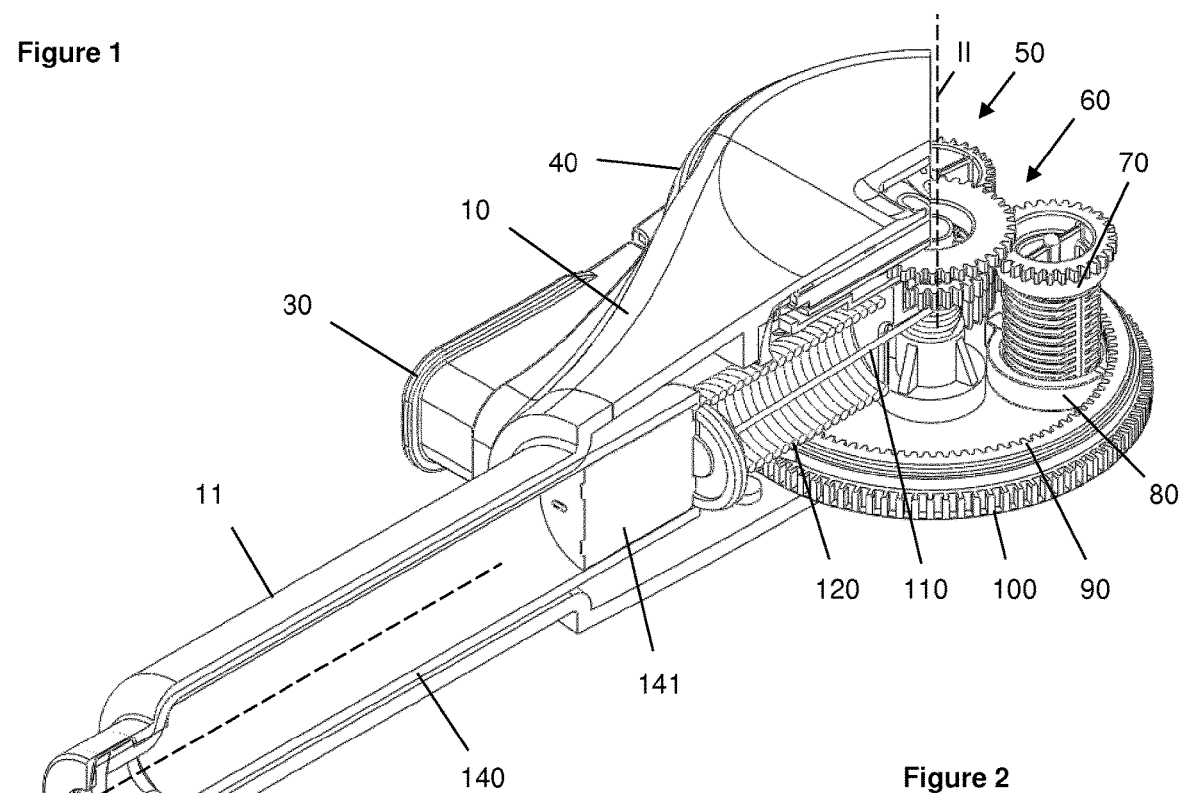
FIG. 1 shows a cut away view of the drug delivery device of the present disclosure.
Figure 2:
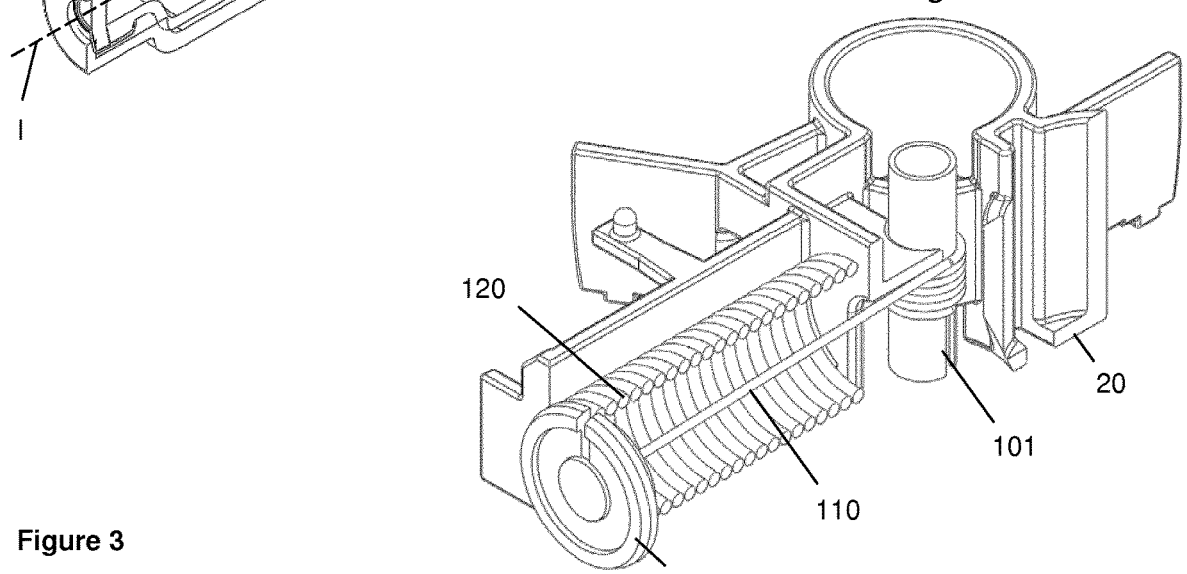
FIG. 2 shows a cut away view of the cable and spring of the device of FIG. 1.

The mechanism comprises the following key components as depicted in FIG. 1: a housing 10, a chassis 20, a dose button 30, a dose selector in the form of a dial grip 40, a dose counter mechanism 50 with a units number wheel 51 and a tens number wheel 52, a clutch 60, a last dose spool 70, a last dose nut 80, a dose ring gear 90, a release gear 100, a cable 110 with a piston 111 or bearing disc, a piston spring 120, a clutch lever 130 with and a cartridge 140.

The medicament cartridge 140 is housed within a cartridge holder component 11 of housing 10. The cartridge holder 11 is rigidly connected to the housing 10 of the pen injector during assembly. The piston 111 is a bearing component located on the main axis I of the pen injector, and is rigidly connected to the cable 110 and the piston spring 120 on its proximal face, and on its distal face abuts the bung 141 of the medicament cartridge 140. The proximal end of the piston spring 120 reacts on the chassis 20.

Figure 5:
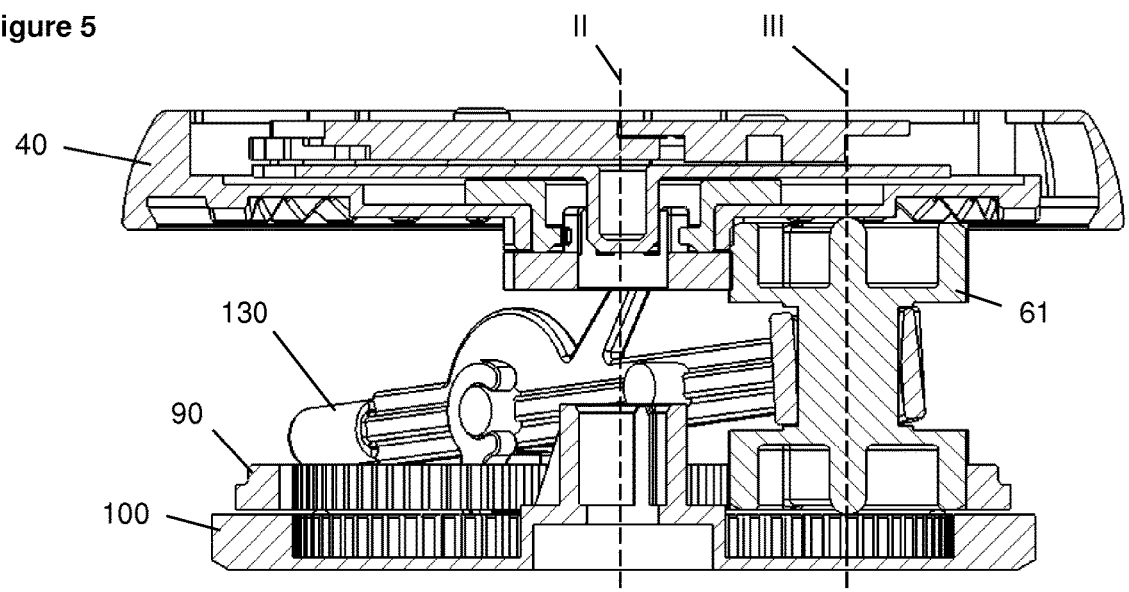
FIG. 5 shows a cut away view of the release mechanism during dose setting of the device of FIG. 1.
Figure 6:
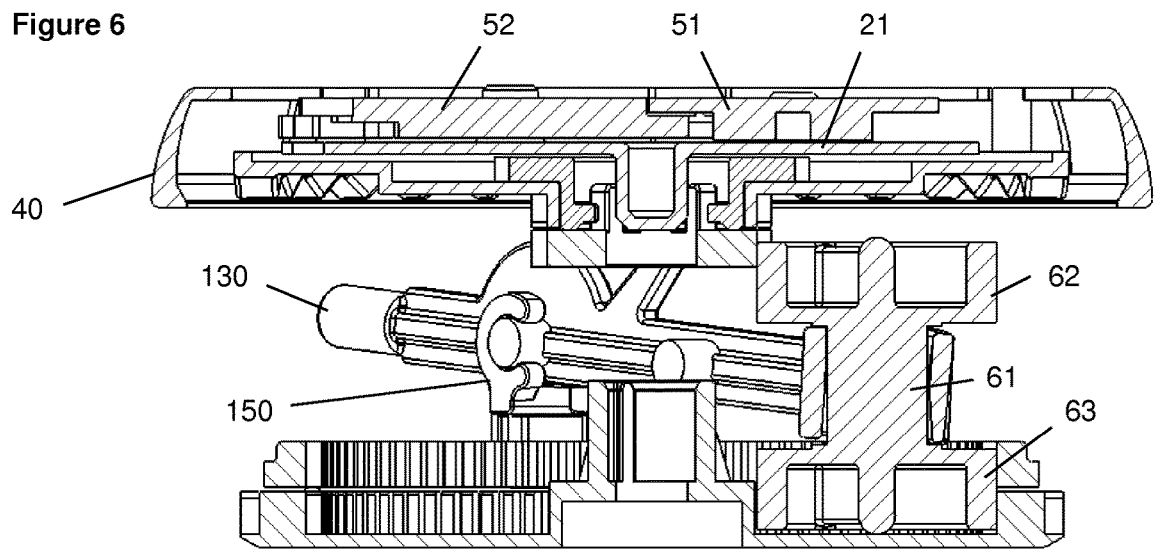
FIG. 6 shows a cut away view of the release mechanism during dose dispensing of the device of FIG. 1.

The proximal end of the cable 110 is terminated on and wrapped around a cable spool 101 of the release gear 100. As the cable spool 101 rotates, a controlled length of the cable 110 is released, forced by the action of the piston spring 120 via the piston 111, causing the piston 111 to advance into the medicament cartridge 140 and dispel some of the medicament. The cable spool 101 is attached and locked in rotation to the release gear 100. The release gear 100 is able to rotate relative to the chassis 20 and the dose counter mechanism 50 about a fixed axis II, perpendicular to the main medicament cartridge axis I. The amount that the release gear 100 rotates during dispense of a dose is defined by the user, and controlled by the release mechanism. This consists of the dose ring gear 90, a clutch gear 61 with a first gear wheel 62 and a second gear wheel 63 connected via a shaft portion, a clutch lever 130, the dial grip 40 and dose stop element 150. As can be seen in FIGS. 5 and 6, the clutch gear 61 has a rotational axis III which is parallel to and off-set from the rotational axis II of the release gear 100.

The clutch lever 130 is pivotably supported in the chassis 20 such that actuation of the button 30 swivels the clutch lever 30, thus raising or lowering the clutch gear 61 as shown in FIGS. 5 and 6 via a sleeve-like end of the clutch lever 130 supporting the clutch gear 61. The opposite end of clutch lever 130 actuates stop element 150 by raising it from the blocking position in which release member 100 is prevented from rotation for dose dispensing or lowering it into the locking position after dispensing.

Figure 3:
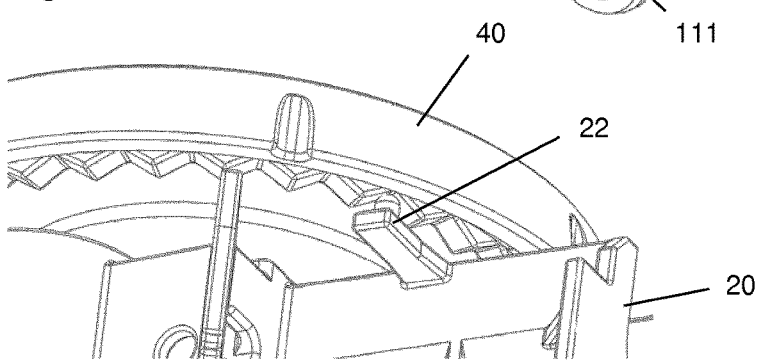
FIG. 3 shows a detail view of the clicker mechanism of the device of FIG. 1.
Figure 4A:
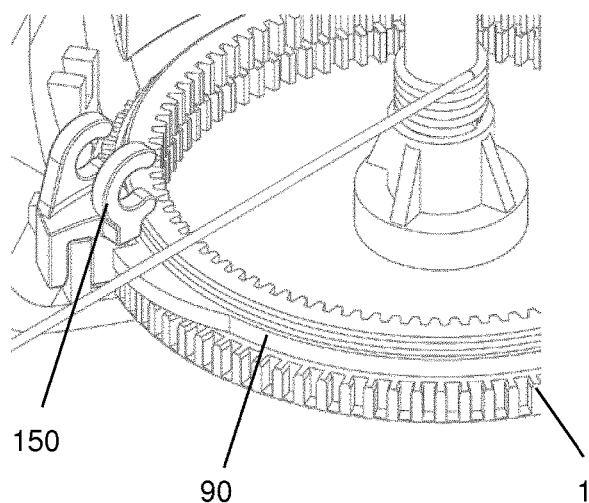
FIG. 4a shows a partial section view of the release mechanism of the device of FIG. 1 before dialing.
Figure 4B:
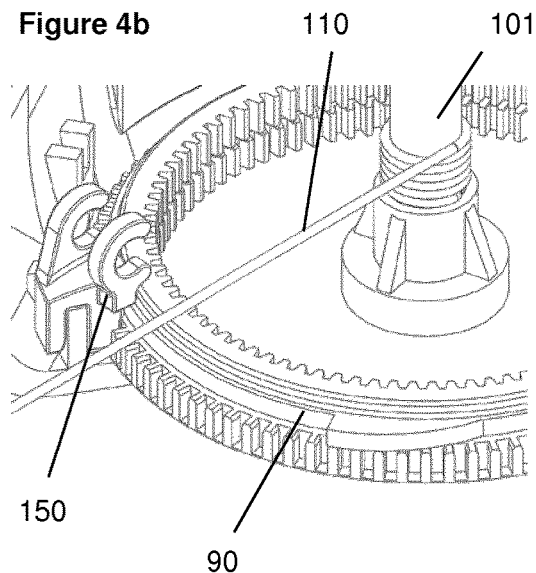
FIG. 4b shows a partial section view of the release mechanism of the device of FIG. 1 during dialing.

When the device is in its "dose setting mode" as shown in FIG. 5, i.e. the button 30 is not pressed by the user, the teeth of clutch gear 61 are engaged with the dial grip 40 and the dose ring gear 90. This engagement causes the dose stop face on the dose ring gear 90 to be rotated away from the dose stop element 150 as the dose is dialled. The position of the dial grip 40 mid-dose is controlled by a dial clicker element 22 which is biased to single-unit detent positions on the dial grip 40 (see FIG. 3). Each of these detent positions corresponds to a single-unit during dialling. The set dose can be dialled both up and down (increasing and decreasing the dose number). An audible click will be produced by the dial clicker, once per unit increment.

The rotational position of release gear 100 is locked via the dose stop element 150 to the housing 10 and chassis 20 throughout dose setting mode and in storage. A maximum, fixed dose limit stop feature between dose ring gear 90 and dose stop element 150 ensures the dose ring gear 90 is not dialed above the maximum permissible dose.

To dispense the user-selected dose, the dose button 30 is pressed in, acting on the clutch lever 130, causing it to rotate about its central pivot and move the clutch gear 61 axially into the dispense position (see FIG. 6). In the dispense position, the clutch gear 61 is engaged with the release gear 100 and the dose ring gear 90, and disengaged from the dial grip 40. The axial movement of the clutch gear 61 is limited by features which act on the release gear 100 and the dial grip 40.

Figure 7A:
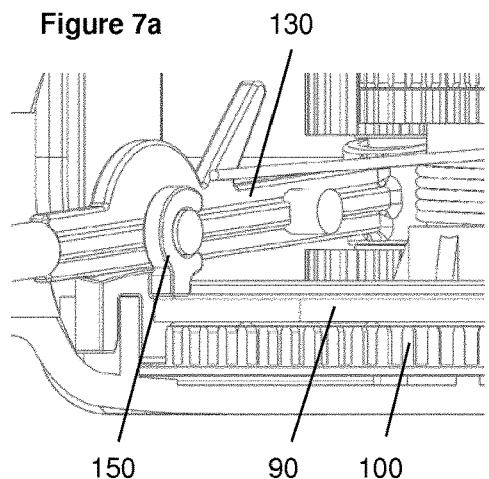
FIGS. 7a & b show partial section view of the dose stop of the device of FIG. 1 during dose setting and dose dispensing.
Figure 7B:
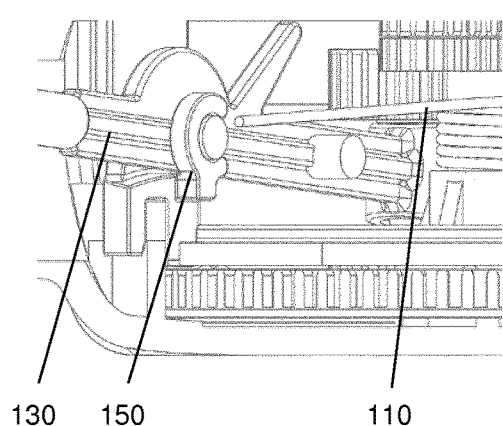

The order in which the clutch gear 61 disengages and engages with the other release mechanism components is important to ensure that the spring energy is not released in an unsafe manner. As the clutch lever 130 moves from the set position, it first locks the rotation of the dial grip 40 by moving the dial clicker into a position whereby it requires a very high torque to dial either up or down. As the clutch lever 130 continues to move it causes the clutch gear 61 to axially engage the release gear 100. The clutch gear 61 and the release gear 100 have chamfered teeth for ease of engagement to accommodate moulding and positional tolerances. As the clutch lever 130 continues to move further, it causes the clutch gear 61 to disengage from the dial grip 40 so that the last dose mechanism is not rewound and the dial grip 40 does not spin during dispense (preventing the user from jamming the device by touching it). Finally, the clutch lever 130 causes the dose stop element 150 to disengage from the release gear 100 (see FIG. 7), allowing the cable spool 101 and the release gear 100 to rotate, releasing some cable 110 and permitting the piston spring 120 to move the bung 141 by piston 111. The cable spool 101 of the release gear 100 rotates (keyed to the dose ring gear 90) until the stop face on the dose ring gear 90 contacts the dose stop element 150, preventing any further rotation and ending dispense.

When the dose button 30 is released after the dose has been expelled, the action of the release mechanism is reversed. The dose stop element 150 re-engages with the release gear 100, then the clutch gear 61 engages with the dial grip 40, then the clutch gear 61 disengages with the release gear 100, and finally the dial clicker is released, allowing the dial grip 40 to be dialed again.

Preferably, there is a return spring integrated into the clutch lever 130 that provides the return force to move the components during this operation. A separate integrated spring on the dose button 30 returns it to its default position. Both springs act on the mechanism chassis 20.

Figure 8:
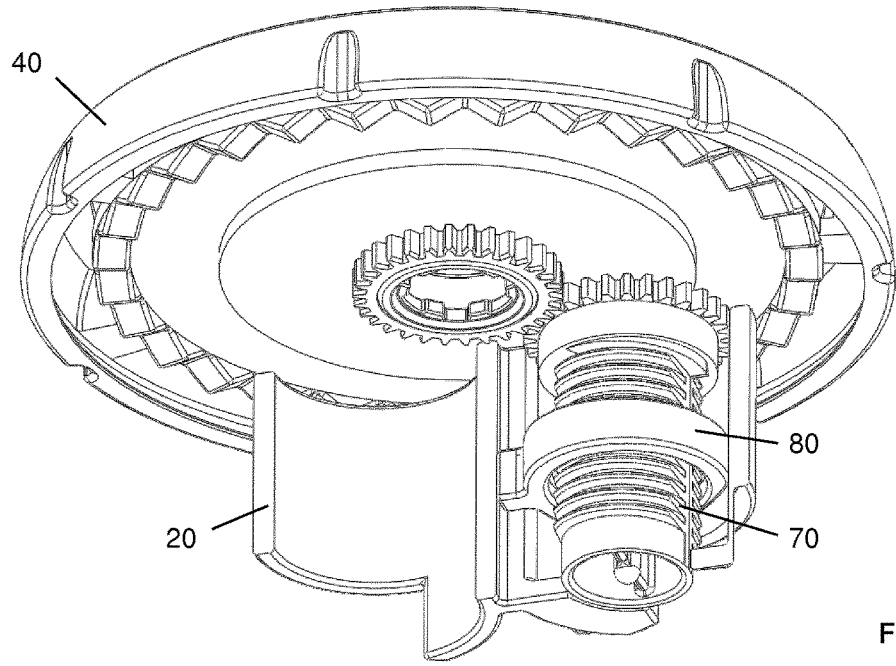
FIG. 8 shows a cut away view of the last dose lock-out mechanism of the device of FIG. 1.
Figure 9:
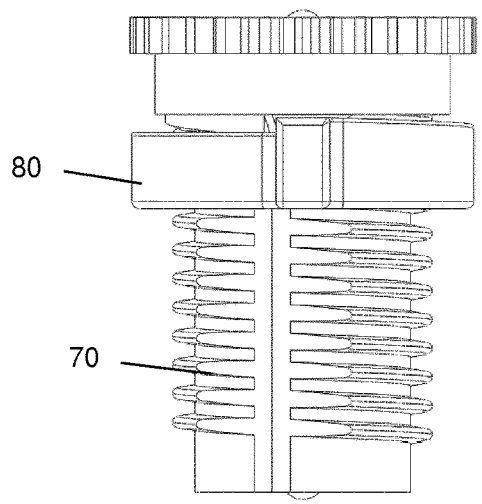
FIG. 9 shows a view of the last dose nut engaged with the last dose spool.

When the medicament cartridge 140 has been emptied, the mechanism locks to prevent the user from setting another dose. As shown in FIGS. 8 and 9, the last dose spool 70 is restrained in the chassis 20 so that it is only able to rotate. It is geared to the dial grip 40 assembly. The last dose nut 80 is engaged with the thread on the last dose spool 70 and prevented from rotating by a spline engagement with the chassis 20. When a dose is dialed, the dial grip 40 rotation causes the last dose spool 70 to rotate via their geared engagement. This rotation causes the last dose nut 80 to move axially up the thread of the last dose spool 70. When a dose is dispensed, as the dial grip 40 is stationary, the last dose mechanism is also held stationary. Eventually, as the total number of doses dialed reaches the capacity of the medicament cartridge, the last dose nut 80 is so far up the thread on the last dose spool 70 that corresponding stop faces on the two components contact each other. This prevents the last dose spool 70 rotating and, therefore, prevents the dial grip 40 rotating, locking out the device.

Figure 10A:
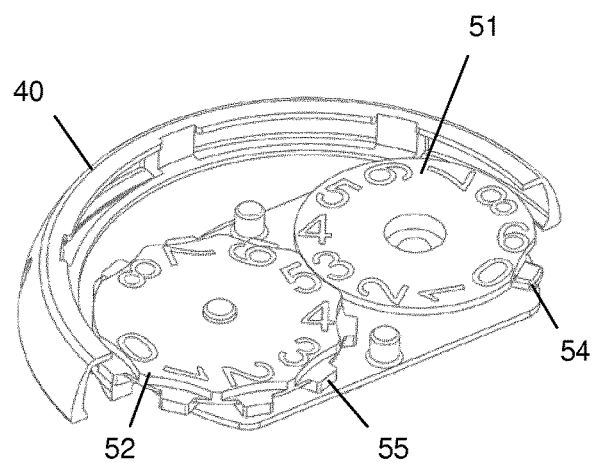
FIGS. 10a, b show top and bottom views of the dose counter mechanism.
Figure 10B:
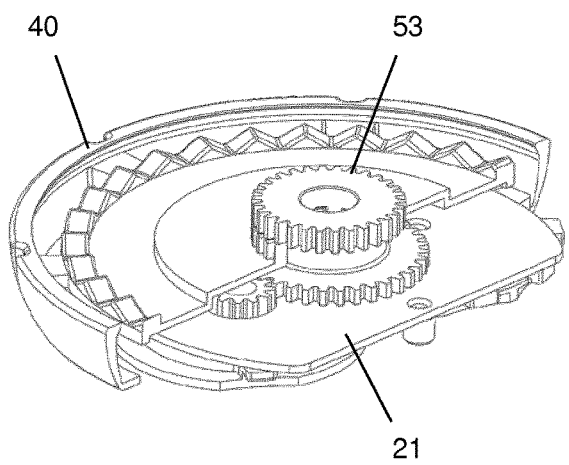

The size of the dialed dose is displayed to the user via a dose counter mechanism 50. This consists of the following components: a counter drive gear 53 with a smaller pinion and a larger pinion, the units number wheel 51, and the tens number wheel 52 (see FIGS. 10a, b). The mechanism is clutched to and is actuated by the dial grip 40 during dose setting, and is de-clutched from the dial grip 40 and actuated by the release gear 100 during dispense mode, both via the clutch gear 61. This ensures the remaining dose is displayed throughout the whole dispense operation.

The counter mechanism is situated in a recess within the dial grip 40. The units number wheel 51 has gear teeth that are permanently engaged with the counter drive gear 53, and a protrusion 54 (driving dog) that acts on the gear tooth-like features 55 (corresponding driven dogs) on the tens number wheel 52. The counter chassis 21 allows the number wheel axes to remain fixed relative to the device housing 10 while the dial grip 40 rotates around them.

Between indexed movement, the tens number wheel 52 is locked from rotating by scalloped recesses on the tens number wheel 52 which are restrained against the circular outer diameter of the units number wheel 51. The tens number wheel 52 is indexed to display the next number by the rotating action of the protrusion on the units number wheel 51 which engage on every rotation of the units number wheel 51. The counter drive gear 53 is in permanent toothed engagement with the clutch gear 61 so that it is rotated during dose setting and dispensing.

As an alternative embodiment the aforementioned device with the cable 110 can also be embodied as a timing belt (not shown). This alternative concept differs predominantly as described below. In this embodiment, the cable 110 and cable spool 101 are replaced with a toothed timing belt, and a toothed belt drum. This has advantages in terms of assembly and robustness in use. The belt drum increases the radius of curvature of the timing belt, thus reducing the stress that it is subjected to. The piston may be of a different design to allow integration with the timing belt. The timing belt has toothed regions at both ends of a plain cross section region, which makes up the majority of the length of the belt. The toothed regions allow permanent attachment to the piston at the distal end and the belt drum at the proximal end of the device. The plain region is wrapped around approximately 75% of the belt drum, and then runs down the inside of the piston spring 120 to the piston. The inner surface of the belt drum is in toothed engagement with the smaller pinion region of the release gear 100.

This alternative embodiment shares the other major functionality with the embodiment comprising the cable 110. This includes, but is not limited to: the dialing and dose setting mechanism, action of the clutch gear 61, zero and maximum unit dose stops, last dose lockout and dose display.

| Reference Numerals: | |
| --- | --- |
| 10 | housing |
| 11 | cartridge holder |
| 20 | chassis |
| 21 | counter chassis |
| 30 | dose button (trigger) |
| 40 | dial grip (dose selector) |
| 50 | dose counter mechanism |
| 51 | units number wheel |
| 52 | tens number wheel |
| 53 | counter drive gear |
| 54 | protrusion (driving dog) |
| 55 | tooth-like feature (driven dog) |
| 60 | clutch |
| 61 | clutch gear |
| 62 | first gear wheel |
| 63 | second gear wheel |
| 70 | last dose spool |
| 80 | last dose nut |
| 90 | dose ring gear |
| 100 | release gear |
| 101 | cable spool |
| 110 | cable |
| 111 | piston |
| 120 | piston spring |
| 130 | clutch lever |
| 140 | cartridge |
| 141 | bung |
| 150 | dose stop element |
| I | main axis |
| II | axis of rotation |
| III | axis of clutch gear |

The invention claimed is:

1. A drug delivery device for selecting and dispensing a number of user variable doses of a medicament, the drug delivery device comprising:
    a housing;
    a dose selector operable to set a dose by rotation relative to the housing;
    a release member operable to control movement of a piston in a dispensing direction;
    a display comprising at least one number wheel or at least one number sleeve; and
    a spring acting on the piston, wherein a cable is attached to the piston and to a cable spool of the release member, such that upon rotation of the release member the piston is allowed to be pushed by the spring,
    wherein the release member rotates, during dose dispensing, an angle corresponding to the dose set by the dose selector to allow the piston to move in the dispensing direction,
    wherein the drug delivery device further comprises a clutch mechanism which rotationally couples the at least one number wheel or the at least one number sleeve to the dose selector and de-couples the at least one number wheel or the at least one number sleeve from the release member during dose setting, and which rotationally de-couples the at least one number wheel or the at least one number sleeve from the dose selector and couples the at least one number wheel or the at least one number sleeve to the release member during dose dispensing.

2. The drug delivery device according to claim 1, wherein the clutch mechanism is operable to be switched between a dose setting position and a dose dispensing position, wherein, when the clutch mechanism is in its dose setting position, the at least one number wheel or the at least one number sleeve is rotationally coupled via the clutch mechanism to the dose selector and the at least one number wheel or the at least one number sleeve is rotationally de-coupled from the release member, and
    wherein, when the clutch mechanism is in its dose dispensing position, the at least one number wheel or the at least one number sleeve is rotationally de-coupled from the dose selector and the at least one number wheel or the at least one number sleeve is rotationally coupled via the clutch mechanism to the release member.

3. The drug delivery device according to claim 1, wherein the display comprises the at least one number wheel, wherein the at least one number wheel comprises a units number wheel and a tens number wheel, and wherein the units number wheel is coupled to the tens number wheel by a gear mechanism, and wherein the gear mechanism comprises a driving dog provided on the units number wheel and a plurality of corresponding driven dogs provided on the tens number wheel.

4. The drug delivery device according to claim 3, wherein the units number wheel comprises one single driving dog and is provided with FIGS. 0 to 9.

5. The drug delivery device according to claim 3, wherein the units number wheel comprises a raised circular blocking disc that locks the tens number wheel in position between steps of intermittent rotary motion of the tens number wheel.

6. The drug delivery device according to claim 1, further comprising a dose ring gear which is rotationally coupled to the dose selector during dose setting and which is rotationally coupled to the release member during dose dispensing.

7. The drug delivery device according to claim 6, wherein the dose ring gear is permanently rotationally coupled to the at least one number wheel or the at least one number sleeve.

8. The drug delivery device according to claim 6, wherein the clutch mechanism rotationally couples the dose ring gear to the at least one number wheel or the at least one number sleeve, rotationally couples the dose ring gear to the dose selector during dose setting, and rotationally couples the dose ring gear to the release member during dose dispensing.

9. The drug delivery device according to claim 1, wherein the clutch mechanism comprises a clutch gear having a first gear wheel and a second gear wheel which is rotationally constrained to the first gear wheel.

10. The drug delivery device according to claim 9, further comprising a dose ring gear which is rotationally coupled to the dose selector during dose setting and which is rotationally coupled to the release member during dose dispensing, wherein the clutch gear is axially movable between a dose setting position, in which the first gear wheel is rotationally coupled to the dose selector and the at least one number wheel or the at least one number sleeve, and in which the second gear wheel is rotationally coupled to the dose ring gear, and a dose dispensing position, in which the first gear wheel is rotationally coupled to the at least one number wheel or the at least one number sleeve, and in which the second gear wheel is rotationally coupled to the dose ring gear and the release member.

11. The drug delivery device according to claim 10, wherein the clutch gear is rotatable about a first axis and wherein the dose selector, the dose ring gear and the release member are rotatable about a second axis which is parallel to and offset from the first axis.

12. The drug delivery device according to claim 1, further comprising a trigger for actuating the clutch mechanism, the trigger comprising a clutch lever pivot-mounted within the housing.

13. The drug delivery device according to claim 12, wherein the clutch lever comprises a guiding sleeve at least partially surrounding a part of the clutch mechanism for axially displacing the clutch mechanism upon actuation of the trigger.

14. The drug delivery device according to claim 1, further comprising a stop element preventing rotation of the release member during dose setting and allowing rotation of the release member during dose dispensing.

15. The drug delivery device according to claim 1, further comprising a cartridge containing a medicament.

16. The drug delivery device according to claim 15, wherein the medicament comprises a pharmaceutically active compound.

* * * * *

UNITED STATES PATENT AND TRADEMARK OFFICE
CERTIFICATE OF CORRECTION

PATENT NO. : 10,799,641 B2
APPLICATION NO. : 15/533771
DATED : October 13, 2020
INVENTOR(S) : Joseph Butler et al.

Page 1 of 1

It is certified that error appears in the above-identified patent and that said Letters Patent is hereby corrected as shown below:

In the Specification

Column 4, Line 42, delete "FIGS." and insert -- figures --

Column 4, Line 44, delete "FIGS." and insert -- figures --

In the Claims

Column 15, Line 3, Claim 4, delete "FIGS." and insert -- figures --

Signed and Sealed this
Fifteenth Day of December, 2020

Andrei Iancu
*Director of the United States Patent and Trademark Office*